(12) United States Patent
Cho et al.

(10) Patent No.: US 9,060,700 B2
(45) Date of Patent: Jun. 23, 2015

(54) MEDICAL MEASUREMENT DEVICE FOR BIOELECTRICAL IMPEDANCE MEASUREMENT

(75) Inventors: Ok Kyung Cho, Schwerte (DE); Yoon Ok Kim, Schwerte (DE)

(73) Assignee: Ingo FLORE, Dortmund (DE)

( * ) Notice: Subject to any disclaimer, the term of this patent is extended or adjusted under 35 U.S.C. 154(b) by 403 days.

(21) Appl. No.: 12/733,551

(22) PCT Filed: Sep. 8, 2008

(86) PCT No.: PCT/EP2008/007331
§ 371 (c)(1),
(2), (4) Date: Apr. 30, 2010

(87) PCT Pub. No.: WO2009/033625
PCT Pub. Date: Mar. 19, 2009

(65) Prior Publication Data
US 2010/0234701 A1   Sep. 16, 2010

(30) Foreign Application Priority Data

Sep. 7, 2007   (DE) .......................... 10 2007 042 550

(51) Int. Cl.
*A61B 5/05*   (2006.01)
*A61B 5/0404*   (2006.01)
(Continued)

(52) U.S. Cl.
CPC ................ *A61B 5/0404* (2013.01); *A61B 5/01* (2013.01); *A61B 5/0537* (2013.01); *A61B 5/14532* (2013.01); *A61B 5/14552* (2013.01); *A61B 5/6826* (2013.01); *A61B 5/6838* (2013.01); *A61B 5/6887* (2013.01); *A61B 5/7257* (2013.01)

(58) Field of Classification Search
CPC .... A61B 5/0205; A61B 5/053; A61B 5/0531; A61B 5/0537; A61B 5/14532
USPC .................................. 600/301, 310, 335, 547
See application file for complete search history.

(56) References Cited

U.S. PATENT DOCUMENTS 3,229,686 A * 1/1966 Edmark, Jr. ................... 600/502
3,805,795 A   4/1974 Denniston et al.
(Continued)

FOREIGN PATENT DOCUMENTS

DE   35 33 912   4/1987
DE   19519125   11/1996
(Continued)

OTHER PUBLICATIONS

International Search Report.
(Continued)

*Primary Examiner* — Max Hindenburg
*Assistant Examiner* — Jonathan M Foreman
(74) *Attorney, Agent, or Firm* — Collard & Roe, P.C.

(57) ABSTRACT

The invention relates to a medical measuring device having an impedance measurement unit (100) for detecting an impedance measurement signal from the skin surface (200) of a patient to be examined via at least one measurement electrode pair (3). According to the invention, the distance between the electrodes of the measurement electrode pair (3) is from a few millimeters to several centimeters such that, during the measurement process, both electrodes of the measurement electrode pair (3) for locally detecting the impedance measurement signal contact the same region of the skin surface (200) of the patient at the same time.

16 Claims, 3 Drawing Sheets

Figure 1:
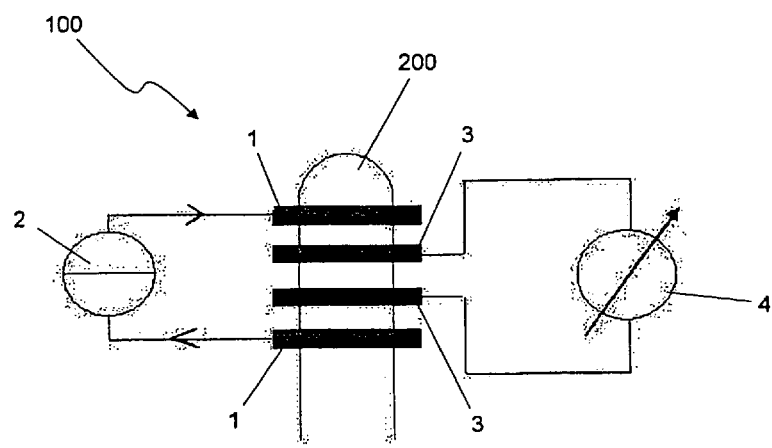

(51) Int. Cl.
*A61B 5/01* (2006.01)
*A61B 5/053* (2006.01)
*A61B 5/145* (2006.01)
*A61B 5/1455* (2006.01)
*A61B 5/00* (2006.01)

(56) References Cited

U.S. PATENT DOCUMENTS

| | | | |
|---|---|---|---|
| 3,958,560 A | 5/1976 | March | |
| 4,907,596 A | 3/1990 | Schmid et al. | |
| 4,911,167 A | 3/1990 | Corenman et al. | |
| 4,928,014 A | 5/1990 | Rosenthal | |
| 4,934,382 A | 6/1990 | Barone, Jr. | |
| 4,938,218 A | 7/1990 | Goodman et al. | |
| 4,960,126 A | 10/1990 | Conlon et al. | |
| 5,153,426 A | 10/1992 | Konrad et al. | |
| 5,191,891 A | 3/1993 | Righter | |
| 5,237,178 A | 8/1993 | Rosenthal et al. | |
| 5,259,381 A | 11/1993 | Cheung et al. | |
| 5,309,916 A | 5/1994 | Hatschek | |
| 5,353,790 A | 10/1994 | Jacques et al. | |
| 5,431,170 A | 7/1995 | Mathews | |
| 5,515,847 A | 5/1996 | Braig et al. | |
| 5,676,143 A | 10/1997 | Simonsen et al. | |
| 5,682,902 A * | 11/1997 | Herleikson | 600/521 |
| 5,771,891 A * | 6/1998 | Gozani | 600/347 |
| 5,795,305 A | 8/1998 | Cho et al. | |
| 5,924,996 A | 7/1999 | Cho et al. | |
| 6,041,247 A | 3/2000 | Weckstrom et al. | |
| 6,128,518 A * | 10/2000 | Billings et al. | 600/345 |
| 6,159,147 A | 12/2000 | Lichter et al. | |
| 6,190,325 B1 | 2/2001 | Narimatsu | |
| 6,230,035 B1 | 5/2001 | Aoyagi et al. | |
| 6,289,230 B1 | 9/2001 | Chaiken et al. | |
| 6,331,162 B1 | 12/2001 | Mitchell | |
| 6,714,814 B2 | 3/2004 | Yamada et al. | |
| 6,763,256 B2 | 7/2004 | Kimball et al. | |
| 6,790,178 B1 | 9/2004 | Mault et al. | |
| 6,819,950 B2 | 11/2004 | Mills | |
| 6,873,865 B2 | 3/2005 | Steuer et al. | |
| 7,215,991 B2 | 5/2007 | Besson et al. | |
| 8,046,059 B2 | 10/2011 | Cho et al. | |
| 2001/0012916 A1 | 8/2001 | Deuter | |
| 2002/0087087 A1 | 7/2002 | Oka et al. | |
| 2003/0009111 A1* | 1/2003 | Cory et al. | 600/547 |
| 2003/0036685 A1 | 2/2003 | Goodman | |
| 2003/0055324 A1 | 3/2003 | Wasserman | |
| 2003/0109901 A1 | 6/2003 | Greatbatch | |
| 2004/0034293 A1 | 2/2004 | Kimball | |
| 2004/0116784 A1 | 6/2004 | Gavish | |
| 2004/0122336 A1* | 6/2004 | Jang et al. | 600/547 |
| 2004/0152957 A1 | 8/2004 | Stivoric et al. | |
| 2004/0162493 A1 | 8/2004 | Mills | |
| 2004/0181132 A1 | 9/2004 | Rosenthal | |
| 2004/0225209 A1 | 11/2004 | Cho et al. | |
| 2005/0013999 A1 | 1/2005 | Wakefield et al. | |
| 2005/0014999 A1 | 1/2005 | Rahe-Meyer | |
| 2005/0020936 A1 | 1/2005 | Lin | |
| 2005/0078533 A1 | 4/2005 | Vyshedskiy et al. | |
| 2005/0131282 A1 | 6/2005 | Brodnick et al. | |
| 2005/0177062 A1 | 8/2005 | Skrabal et al. | |
| 2005/0192488 A1* | 9/2005 | Bryenton et al. | 600/301 |
| 2005/0261594 A1 | 11/2005 | Banet | |
| 2006/0009697 A1 | 1/2006 | Banet et al. | |
| 2006/0129040 A1* | 6/2006 | Fine et al. | 600/335 |
| 2006/0135857 A1 | 6/2006 | Ho et al. | |
| 2006/0155193 A1 | 7/2006 | Leonardi et al. | |
| 2007/0038048 A1 | 2/2007 | Gerder | |
| 2007/0106139 A1 | 5/2007 | Nagata et al. | |
| 2007/0265533 A1 | 11/2007 | Tran | |
| 2008/0146892 A1 | 6/2008 | LeBoeuf et al. | |
| 2008/0200823 A1 | 8/2008 | Cho et al. | |
| 2008/0275317 A1* | 11/2008 | Cho et al. | 600/310 |
| 2010/0004517 A1 | 1/2010 | Bryenton et al. | |
| 2010/0056880 A1 | 3/2010 | Cho et al. | |
| 2012/0016210 A1 | 1/2012 | Kim et al. | |

FOREIGN PATENT DOCUMENTS

| | | |
|---|---|---|
| DE | 298 11 049 | 12/1998 |
| DE | 298 11 049 | 2/1999 |
| DE | 20 2005 001 894 | 5/2005 |
| EP | 1 317 902 | 6/2003 |
| EP | 1 407 713 | 4/2004 |
| EP | 1 491 134 | 12/2004 |
| WO | 90/04352 | 5/1990 |
| WO | 96/01585 | 1/1996 |
| WO | WO 99/62399 | 12/1999 |
| WO | WO 00/69328 | 11/2000 |
| WO | 01/65810 | 9/2001 |
| WO | 2005/048831 | 6/2005 |
| WO | 2005048831 | 6/2005 |
| WO | WO 2005/077260 | 8/2005 |
| WO | WO 2006/099988 | 9/2006 |
| WO | WO 2007/017266 | 2/2007 |
| WO | 2008/061788 | 5/2008 |
| WO | 2008061788 | 5/2008 |

OTHER PUBLICATIONS

Meir Nitzan, Boris Khanokh, "Infrared radiometry of thermally insulated skin for the assessment of skin blood flow," Optical Engineering 33, 1994, No. 9, pp. 2953-2956.

Cho et al., "Noninvasive Measurement of Glucose by Metabolic Heat Conformation Method," Clinical Chemistry, International Journal of Laboratory Medicine and Molecular Dianostics, 2004, vol. 50, No. 10, pp. 1894-1898.

Lepretre et al., "Effect of Exercise Intensity on Relationship between $VO_{2max}$ and Cardiac Output," Official Journal of the American College of Sports Medicine, 2004, pp. 1357-1363. XP-002428499.

Turner et al., "Effect of dried garlic powder tablets on postprandial increase in pulse wave velocity after a fatty meal: preliminary observations," Scandinavian Journal of Nutrition, 2005, vol. 49, pp. 21-26. XP-008079156.

European Search Report in EP 10 009 799.7, dated Nov. 11, 2010 with English translation of relevant parts.

Tao Dai et al., Blood Characterization From Pulsatile Biompedance Spectroscopy, CCECE 2006 (Canadian Conference on Electrical and Computer Engineering), pp. 983-986, Ottawa, Ontario.

\* cited by examiner

MEDICAL MEASUREMENT DEVICE FOR BIOELECTRICAL IMPEDANCE MEASUREMENT

CROSS REFERENCE TO RELATED APPLICATIONS

This application is the National Stage of PCT/EP2008/007331 filed on Sep. 8, 2008, which claims priority under 35 U.S.C. §119 of German Application No. 10 2007 042 550.5 filed on Sep. 7, 2007. The international application under PCT article 21(2) was not published in English.

The invention relates to a medical measurement device having an impedance measurement unit for detecting an impedance measurement signal on the skin surface of a patient to be examined, by way of at least one measurement electrode pair.

The bioelectrical impedance methods currently in use are used for determining the nutritional state of both healthy and sick persons.

Direct measurement of the body composition is currently only possible in research facilities, by weighing the patient underwater. In so-called hydrostatic weighing, advantage is taken of the fact that fat, muscles, bone, bodily fluids and other components of the body possess different specific densities. Since this measurement method is very complicated and uncomfortable for the patient, other indirect methods for determining body composition are frequently used. One widespread indirect method is measurement of the bioelectrical impedance of the body. In this technique, advantage is taken of the fact that the impedance of the human body is connected with the different conductivities within the body. If a constant alternating current of low amplitude is applied in biological structures, a frequency-dependent impedance can be measured. The human body consists of intracellular and extracellular fluid, which can be viewed as being electrical conductors, and cell membranes, which have a capacitative nature. At low frequencies, around 1 kHz, the current flow takes place mainly through the extracellular fluid, since the cell membranes act as a capacitor, because of their capacitative nature. At high frequencies, the current is also conducted by way of the cell membranes and the intercellular fluid. In the range of high frequencies, the current flow therefore takes place both in ohmic manner, through the extracellular fluid, and in capacitative manner, through the cell membranes and the intracellular fluid. The resulting, measurable alternating current resistance therefore possesses an ohmic component R (resistance) and a capacitative component $X_c$ (reactance), and one speaks of the measurement of the bioelectrical impedance Z. For a long time, attempts have been made to estimate and assess body composition on the basis of the measured resistance and reactance, together with the age, the height, and the gender of the person being examined. This is possible using numerous assumptions: In the human body, the major part of the current applied flows through the fluid contained in the body. With the assumption that the body mass consists of water at precisely 73.2%, the fat-free mass (FFM) can then be estimated from the "measured" total body water (TBW). Once the fat-free mass is known, the fat mass (FM) can be determined quite simply, from the global mass (GM) of the patient.

These known and established techniques therefore determine a global index for the patient being examined. This global index is the result of the integral measurement method that is used in these techniques: Typically, the electrodes are attached to the two hands (determination of the global index of the upper body), or a measurement between a hand and a foot is carried out (global index for the measured side of the body).

The invention is based on the task of making available a measurement device for bioelectrical impedance measurement that is developed further.

The invention accomplishes this task, proceeding from a measurement device of the type indicated initially, in that the distance between the electrodes of the measurement electrode pair amounts to less than a millimeter up to a few centimeters, in such a manner that during the measurement process, the two electrodes of the measurement electrode pair touch the skin surface of the patient in the same region, at the same time, for local determination of the impedance measurement signal.

The measurement device according to the invention is based on a further development of established techniques, in the direction of a local bioelectrical impedance measurement. By means of shortening the distance between the electrodes to the range of less than a millimeter up to a few centimeters, integration does not take place over the entire body, but rather the bioelectrical impedance is recorded locally. According to the invention, all the electrodes touch one and the same local region of the skin surface, i.e. all the electrodes make contact with the same body part (for example hand, finger, foot, or toe) of the patient to be examined.

It is practical if the measurement device according to the invention has a feed electrode pair for applying an alternating current of variable frequency to the body tissue of the patient to be examined, by way of the skin surface, in order to measure the local resistance and reactance, specifically in the region of the skin surface that touches the measurement electrodes.

Preferably, the distance between the feed electrodes, corresponding to the measuring electrodes, amounts to a few millimeters up to a few centimeters. An embodiment in which the measuring and feed electrodes are configured as contact strips that run parallel to one another has proven to be particularly advantageous. This makes it possible to determine the local impedance of the body tissue without distorting influences, for example caused by transition resistance between electrodes and skin surface.

To generate the alternating current of variable frequency, it is practical if the measurement device according to the invention has an alternating current generator. The impedance signal is digitalized by means of an analog/digital converter, and afterwards subjected to a discrete Fourier transformation (DFT). The DFT algorithm then provides the real and imaginary part of the impedance, i.e. the resistance value and the reactance value. These values can be digitally processed further for evaluation.

Preferably, the distance between the electrodes amounts to a maximum of 10 cm, particularly preferably 50 micrometers to 5 cm, further preferably 1000 micrometers to 1 cm, most preferably 1 mm to 5 mm.

By means of the configuration of the measurement device according to the invention, it is possible to determine local changes in impedance over time. For this purpose, it is practical if the measurement device has an evaluation unit connected with the impedance measurement unit. The evaluation unit can be program-controlled, so that evaluation of the impedance measurement signals can be implemented flexibly, by means of software.

For example, the local bioimpedance changes on the basis of the changing amount of blood within a pulse beat, thereby making a determination of the heart rate possible by way of the local bioelectrical impedance. In this connection, the pulse amplitude is determined at the same time, as an important physiological parameter. It has been shown that this pulse amplitude correlates to body temperature, i.e. it is possible to determine the temperature of the body part being examined, using the bioimpedance analysis. Furthermore, the local bioimpedance depends on the amount of fluid, i.e. on the local amount of blood in the tissue being examined, thereby making it possible to determine the local perfusion (the local volume variation caused by perfusion, for example in the form of a volume pulse signal) of the tissue being examined. Finally, the local bioelectrical impedance of the body changes as a function of the intake of nutrients, so that bioimpedance can be used to examine the metabolism, which is known to be determined by the blood glucose level. The measurement device according to the invention thus allows non-invasive monitoring of the blood glucose value, whereby the effect of the glucose and/or the energy demand of the physiological reactions initiated by glucose in the body are investigated. By means of a suitable algorithm that is implemented in the evaluation unit by means of software, it is possible to make statements concerning the blood glucose level based on the recorded impedance measurement signals.

A particularly practical embodiment of the measurement device according to the invention results from a combination with other measurement modalities.

The measurement device according to the invention can additionally be equipped with an optical measurement unit. This unit has a radiation source for irradiating the body tissue being examined with electromagnetic radiation, and at least one radiation sensor for detecting the radiation scattered and/or transmitted by the body tissue. Usual light-emitting diodes or also laser diodes are possible as a radiation source, which emit optical radiation, i.e. light in the corresponding spectral range. It has proven to be particularly advantageous if the radiation absorption in the body tissue being examined is measured, using the device according to the invention, in at least two or, even better, three different light wavelengths, in order to thereby determine the oxygen concentration of the blood and the perfusion of the tissue. The optical measurement unit thus forms a pulse-oximetry unit of the measurement device according to the invention.

According to a practical embodiment, the optical measurement unit of the measurement device according to the invention has at least two radiation sensors for detection of the radiation scattered and/or transmitted by the body tissue, whereby the radiation sensors are disposed at different distances from the radiation source. This opens up the possibility of drawing conclusions concerning the distance traveled by the radiation in the body tissue, in each instance. On this basis, the oxygen concentration in the blood and in the tissue in tissue layers that lie at different depths can be investigated. In this connection, advantage can be taken of the fact that the measurement signals from the tissue layers that lie lower down are more strongly influenced by the arterial blood, while the radiation absorption is more strongly influenced by the blood in the capillary vascular system in the regions close to the surface.

An embodiment of the measurement device according to the invention in which at least two radiation sources are provided, which irradiate different volume regions of the body tissue being examined, is advantageous. In this way, a differential measurement of the light absorption can be implemented in simple manner. This makes it possible to investigate metabolism-induced changes in perfusion of the body tissue being examined, with oxygen-rich or oxygen-poor blood. In this connection, advantage is taken of the fact that the local oxygen consumption changes as a function of the metabolic activity of the tissue. The determination of the changing oxygen consumption in turn permits conclusions with regard to the local energy consumption, which is directly correlated with the oxygen consumption. It is particularly interesting that this in turn permits conclusions concerning the glucose level. Thus, the measurement device according to the invention advantageously permits non-invasive determination of the blood glucose level, as well, by means of an optical measurement. The redundant determination of the blood glucose level by means of the different measurement modalities increases the accuracy and the reliability of the measurement device according to the invention.

The two radiation sources of the optical measurement unit of the measurement device according to the invention should be designed in such a manner that the volume regions irradiated by them, in each instance, are affected differently with regard to the perfusion with oxygen-poor and oxygen-rich blood, respectively. This can be achieved, for example, in that the at least two radiation sources have different spatial emission characteristics. For example, a light emitting diode and a laser that have similar wavelengths (for example 630 nm and 650 nm) can be used as radiation sources. The two radiation sources differ, however, in the aperture angle of their emission. While the light-emitting diode, for example, radiates light into the body tissue being examined at a large aperture angle, the light of the laser diode enters the body tissue at a very small aperture angle. This has the result that different volume regions of the body tissue are detected with the two radiation sources. Because of the large aperture angle, the light-emitting diode detects a larger volume region of the non-perfused epidermis than the laser does. The non-perfused epidermis is practically unaffected by changes in hemoglobin concentration. Accordingly, the intensity of the radiation of the light-emitting diode scattered and/or transmitted by the body tissue is less strongly dependent on a change in the hemoglobin concentration than the intensity of the radiation of the laser. The prerequisite is that the wavelength of the radiation emitted by the two radiation sources, in each instance, is selected in such a manner that the radiation is absorbed to different degrees by the oxyhemoglobin and deoxyhemoglobin, respectively. The wavelength should therefore lie between 600 and 700 nm, preferably between 630 and 650 nm.

According to a practical embodiment, the at least one radiation source is connected with a light-conducting element, for example an optical fiber. The radiation emitted by the radiation source or the radiation sources, respectively, is conducted to the skin surface of the patient to be examined by way of the light-conducting element. The advantageous possibility exists of coupling the radiation of multiple radiation sources, for example multiple LED chips that are bonded to a common substrate into a single light-conducting element. In this connection, the different radiation sources can be coupled with the light-conducting element in different ways. In this way, different emission characteristics of the radiation of the different sources into the body tissue to be examined can be achieved.

The evaluation unit of the measurement device according to the invention can advantageously be utilized also for evaluating the optical measurement signals. For this purpose, it is practical if the evaluation unit is be configured to determine a local metabolic parameter from the radiation of the two radiation sources scattered and/or transmitted by the body tissue. If oxygen is consumed in the body tissue being examined, oxyhemoglobin is converted to deoxyhemoglobin. By means of a comparison of the radiation of the two radiation sources that comes from the different volume regions of the body tissue, the change in the concentration ratio of oxyhemoglobin and deoxyhemoglobin can be determined. This in turn results in the local oxygen consumption, and finally (indirectly), the blood glucose level. Thus, it is practical if the evaluation unit of the measurement device according to the invention is set up to determine the local oxygen consumption and/or the blood glucose level on the basis of the intensities of the radiation of the two radiation sources scattered and/or transmitted by the body tissue.

The functional scope of the measurement device according to the invention is advantageously expanded by means of an EKG unit for detecting an EKG signal by way of two or more EKG electrodes. According to this advantageous further development of the invention, impedance measurement signals, pulse-oximetry signals, and EKG signals, for example, are detected and evaluated in combination, by means of the measurement device.

The evaluation unit of the measurement device can then advantageously be equipped for evaluation of the time progression of the volume pulse signals and the EKG signals. By means of a suitable program control, the evaluation unit of the measurement device according to the invention is able to automatically recognize the R peaks in the EKG signal. In this way, the precise point in time of the heartbeat is determined automatically. Furthermore, because of its program control, the evaluation unit is able to recognize the maxima in the volume pulse signal. Based on the maxima in the volume pulse signal, the time of arrival of a pulse wave triggered by a heartbeat, at the peripheral measurement location detected by the measurement device, can be determined. Thus, finally, the time interval between an R peak in the EKG signal and the subsequent maximum in the volume pulse signal can be determined. This time interval is a measure of the so-called pulse wave velocity. On the basis of the pulse wave velocity, a statement about the blood pressure can be made, on the one hand. This is because a shortening in the pulse wave velocity is accompanied by an increase in blood pressure, while a lengthening in the pulse wave velocity permits the conclusion of a reduction in blood pressure. Furthermore, the pulse wave velocity is dependent on the density of the blood and, in particular, on the elasticity of the blood vessel walls (for example the aorta). In turn, a conclusion concerning arteriosclerosis that might be present can be drawn from the elasticity of the blood vessels.

The absolute values of the heart rate, the heart rate variability, and corresponding arrhythmias of the heart can also be included in the evaluation of the measurement signals. Thus, arrhythmias such as sinus tachycardia, sinus bradycardia, sinus arrest, and so-called escape beats can be automatically determined. Using the EKG signal, statements concerning the time duration of the atrial contraction of the heart during a heartbeat, the time duration of the heart chamber contraction, as well as the duration of relaxation of the heart chamber, etc., can furthermore be determined. Furthermore, preliminary diagnoses concerning so-called blocks in the line of the electrical excitation signals at the heart (AV block, bundle branch block, etc.) and also with regard to perfusion problems or infarctions are possible. Other irregularities in the pulse progression can be determined using the volume pulse signal.

It is practical if at least one of the EKG electrodes of the measurement device according to the invention is simultaneously used as a feed or measurement electrode of the impedance measurement unit.

According to an advantageous embodiment, the measurement device according to the invention comprises an integrated temperature or heat sensor. This sensor can be used to determine the local heat production. In the simplest case, the temperature sensor is configured to measure the surface temperature of the skin at the measurement location. Based on the heat exchange, a conclusion can be drawn with regard to the local metabolic activity. Furthermore, the heat sensor is suitable for determining the local perfusion. With regard to more detailed background information concerning heat measurement, reference is made to the publication by Nitzan et al. (Meir Nitzan, Boris Khanokh, "Infrared Radiometry of Thermally Insulated Skin for the Assessment of Skin Blood Flow," Optical Engineering 33, 1994, No. 9. p. 2953 to 2956).

The combination of the aforementioned measurement methods, namely impedance measurement, oximetry, EKG measurement, and temperature or heat measurement, according to the invention, is particularly advantageous. All the measurement signals can be evaluated and combined by means of the evaluation unit of the measurement device, using a suitable algorithm, in order to examine the metabolism. By means of the combination of the different measurement modalities, great effectiveness and redundancy and thus reliability in the recognition of pathological changes are achieved.

The combination of the different measurement modalities that can be combined in the measurement device according to the invention, as described above, is furthermore advantageous because, as was already mentioned above, this makes non-invasive measurement of the glucose concentration possible. A possible method of procedure in the determination of the blood glucose level by means of the device according to the invention will be explained in greater detail below:

The measurement device according to the invention serves to measure and evaluate data that are influenced by the metabolism. It is directly evident that in this connection, the energy metabolism and the composition of the nutrients taken in by a user of the measurement device play a large role. The nutrients that are involved in the metabolism are known to be essentially carbohydrates, fats, and proteins. For further processing, carbohydrates are converted to glucose, proteins are converted to amino acids, and fats are converted to fatty acids. The energy carriers in turn are converted in the cells of the body tissue, together with oxygen, to produce ATP (adenosine triphosphoric acid), giving off energy. ATP is the actual energy carrier of the body itself. The use of glucose to produce ATP is preferred. However, if the production of ATP from glucose is inhibited (for example due to a deficiency of insulin), increased fatty acid oxidation takes place, instead. However, the oxygen consumption is different in this process.

The reaction of the metabolism of the human body to an intake of nutrients depends, as was mentioned above, on the composition of the nutrients, in characteristic manner. For example, the vascular system of the body reacts as a function of how much energy the body requires to digest the foods that are consumed. The reaction of the body to nutrient intake can be determined on the basis of the pulse wave velocity, which can be determined using the measurement device according to the invention, as well as on the basis of the blood pressure amplitude and the pulse. For this purpose, it is practical if the evaluation unit of the measurement device according to the invention is set up for evaluating the time progression of the pulse wave velocity, and for determining the composition of the nutrients taken in by a user of the measurement device, on the basis of the time progression of the pulse wave velocity since the time of nutrient intake. The pulse wave velocity, as well as the blood pressure amplitude and the pulse, change as soon as the intake of nutrients begins. The maxima and the points in time of the maxima, in each instance, are influenced, in this connection, by the nutrient composition. The progression and the absolute height of the pulse wave velocity, blood pressure amplitude, and pulse can be used to determine the composition of the nutrients taken in, by means of the evaluation unit of the measurement device according to the invention.

The metabolism of the human body is determined essentially by the glucose metabolism in the normal state, i.e. at rest and in the so-called thermoneutral zone. For this reason, the glucose concentration in the cells of the body tissue in this normal state can be described as a pure function of heat production and oxygen consumption. The following applies:

$$[Glu] = f_1(\Delta T, VO_2),$$

where [Glu] stands for the glucose concentration. The heat production $\Delta T$ can be determined by means of the heat sensor of the measurement device according to the invention, for example from the difference between the arterial temperature and the temperature that the skin surface would reach in the case of perfect thermal insulation ($\Delta T = T_\infty - T_{artery}$). f1 ($\Delta T$, $VO_2$) indicates the functional dependence of the glucose concentration on the heat production and on the oxygen consumption. The oxygen consumption results from the difference between venous and arterial oxygen saturation and perfusion, as was explained above. To determine the glucose concentration during or immediately after nutrient intake, however, a correction term has to be taken into consideration, which reproduces the proportion of the fat metabolism in the energy metabolism. The following then applies:

$$[Glu] = f_1(\Delta T, VO_2) + X^* f_2(\Delta T, VO_2)$$

X is a factor that is negative after nutrient intake. In this connection, X depends on the composition of the nutrients taken in. In particular, X depends on the ratio at which fat and carbohydrates are involved in the metabolism. The factor X can be determined, as was described above, using the time progression of the pulse wave velocity. X is 0 if pure carbohydrates or glucose are consumed directly. The amount of X increases, the greater the proportion of fat in the nutrients taken in. To determine the correction factor X from the time progression of the pulse wave velocity, the blood pressure amplitude and/or the pulse, a calibration of the measurement device according to the invention for adaptation to the user of the device, in each instance, will normally be necessary. $f_2$ ($\Delta T$, $VO_2$) indicates the functional dependence of the glucose concentration on the heat production and on the oxygen consumption, for the fat metabolism.

The evaluation unit of the measurement device according to the invention can thus be set up for determining the local glucose concentration from the local oxygen consumption and the local heat production. For this purpose, the measurement device must have the suitable measurement modalities. The determination of oxygen consumption, as was explained above, can take place by means of a combination of oximetry with a bioelectrical impedance measurement. To determine the heat production, a suitable heat sensor is then additionally required. Finally, in order to be able to calculate the glucose concentration according to the functional relationship indicated above, the correction factor X should also be determined, for example from the time progression of the pulse wave velocity. This can take place, as was also explained above, by means of a combined measurement of EKG signals and pulse-oximetry signals. Therefore, in order to determine the glucose concentration, it is practical if the measurement device according to the invention combines a bioelectrical impedance measurement unit, a pulse oximeter, an EKG unit, and a heat sensor.

The method outlined above at first only allows a determination of the intracellular glucose concentration. The following relationship with the blood glucose concentration exists, in simplified form:

$$[Glu]_{cell} = a + b^* \ln(c^* [Glu]_{blood})$$

The constants a, b, and c depend on the individual physiology of the user of the measurement device. Thus, the evaluation unit of the measurement device according to the invention can furthermore be set up to determine the blood glucose level from the local glucose concentration, whereby parameters that depend on the physiology of the user of the measurement device have to be taken into consideration. These parameters can be determined by means of corresponding calibration, for example by means of a comparison with blood glucose values determined invasively, in conventional manner.

It is practical to equip at least one, but preferably all the measurement modalities of the measurement device according to the invention with a low-pass filter and/or a 50/60 Hz filter, to free them of superimposed electromagnetic interference. This can be done either by means of suitable electronic wiring (for example ahead of the analog/digital converter) or within the measurement data processing by means of the evaluation unit.

An embodiment of the measurement device according to the invention in which all the measurement modalities are combined into a compact sensor unit is particularly preferred, specifically in such a manner that all the measurements take place in the same region of the skin surface of the patient to be examined. In this manner, a compact sensor unit is created, which yields a plurality of diagnostic measurement values. These can be evaluated individually or in combination, in order to obtain diagnostically conclusive information concerning the health state of the patient being examined, quickly and reliably. The compact sensor unit can be pre-fabricated, as a completely functional part, in large numbers, in cost-advantageous manner, and can be integrated into diagnosis devices of the most varied kinds. The actual measurement can be carried out in particularly simple and convenient manner. For this purpose, all that needs to be done is to bring the surface of the sensor housing, where the electrodes of the impedance measurement unit and the EKG unit are situated, for example, into contact with the skin in the region of the body tissue to be examined. This can take place, for example, by simply placing a finger of the patient on the housing surface of the sensor unit. The impedance measurement and the EKG derivation then take place at the same time, by way of the skin location touching the sensor unit.

The measurement device according to the invention can be integrated into a mobile monitoring device in which the medical measurement modalities mentioned above, individually or in combination, form the data recording unit for measurement data recording, and in which the program-controlled evaluation unit for evaluation of the recorded measurement data is provided. A memory unit serves to store the recorded and/or calculated/evaluated data. A display unit is provided to visualize the recorded and/or evaluated data. A data transmission unit serves to transmit the recorded data and/or the calculated/evaluated data to external devices. In this connection, this can be a usual wired interface or also a wireless interface (for example according to the Bluetooth standard). The data stored in the memory unit of the monitoring device can be read out and evaluated by a treating physician, in order to monitor the progression of treatments of the patient. The data transmission interface of the monitoring device can be used to transmit data stored in the memory unit of the monitoring device to a personal computer of the physician. However, it is practical that remote data transmission of the diagnostic data detected and evaluated by means of the sensor unit can also take place. Data transmission can take place, for example, by way of a data network (Internet). Alternatively, the diagnostic data can be transmitted by way of a mobile radio network. The raw measurement signals or the evaluated diagnostic data can be transmitted, for example, to a central location ("healthcare center") for a more detailed analysis and documentation, and for monitoring of the development over time of individual values. There, the data are evaluated, for example, by means of suitable analysis algorithms, if necessary taking into consideration patient data stored there (including information concerning chronic illnesses or prior illnesses). The result, in turn, can be sent back by way of the data network or communication network, in each instance, in order to inform the user of the measurement device accordingly, about his state of health. From the central location, other targeted measurements by means of the sensor unit according to the invention can also be initiated, if necessary. Furthermore, for the purpose of an expanded anamnesis, queries to the patient concerning the evaluation results can be transmitted by way of the data network or communication network. If indications of a medical emergency become evident from the measurement and evaluation results, the required measures (for example automatic alarm to emergency services) can be initiated immediately.

Another advantage of remote data transmission is that the required software for evaluation of the measurement signals does not have to be implemented in the device itself, but rather merely has to be kept on hand and administered at the central location where the data are received.

According to a preferred embodiment of the measurement device, the data recording unit (the impedance measurement unit), the evaluation unit, the memory unit, the display unit, and the transmission unit are accommodated in a common housing. As a result, the device has a compact structure and can be used at any time and anywhere, as a mobile device. The measurement device can be a stand-alone device, or it can be integrated into an electronic device that can be used in some other way (for example a wristwatch, mobile telephone, MP3 player, digital camera). It is also possible to connect the measurement device according to the invention with any desired device of entertainment or communication technology, for example a desktop, notebook, laptop, mobile telephone, palmtop, or handheld. The use of such a device can quickly, conveniently, and unobtrusively carry out a measurement to determine the physiological parameters that are of interest, at any time. Because of the small size of the sensor system of the measurement device according to the invention, this can also be integrated into any desired accessory, for example eyeglasses, a wristwatch, a piece of jewelry, or the like, or into an article of clothing (so-called "smart clothes").

According to another preferred embodiment of the measurement device according to the invention, a fixation device for fixation of a body part, for example a finger, of the patient to be examined is provided. In the case of impedance measurements and also in the case of pulse-oximetry measurements, the contact pressure of the body tissue (for example the finger) on the optical sensor, i.e. on the measurement and feed electrodes of the impedance measurement unit has a significant influence on the measurement signals. Accordingly, it can be practical to assure a defined contact pressure by means of the fixation device. The fixation device can comprise, for example, an inflatable air cushion that (gently) presses the corresponding body part against the measurement and/or feed electrodes, or against the optical sensors, and fixes it in place there. By means of the fixation, movements of the body part that could distort the measurement result are also advantageously prevented.

In another advantageous embodiment of the measurement device according to the invention, a plurality of feed and/or measurement electrodes is disposed in the form of a matrix. This makes it possible to produce different spatial configurations in the direct current feed and in the voltage measurement. The additional information gained in this connection makes it possible to draw conclusions concerning the pH, the $pCO_2$ value, the $pO_2$ value, as well as the electrolyte metabolism ($Na^+$, $K^+$, $Ca^{2+}$, $Mg^{2++}$ concentration, etc.).

Figure 2:
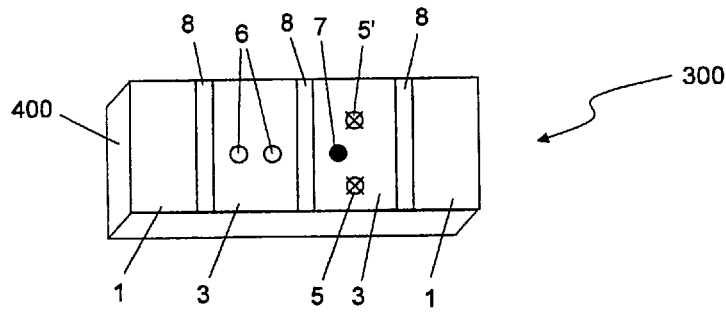
Figure 3:
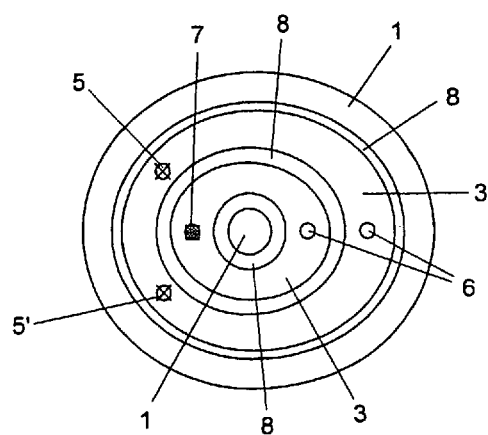
Figure 4:
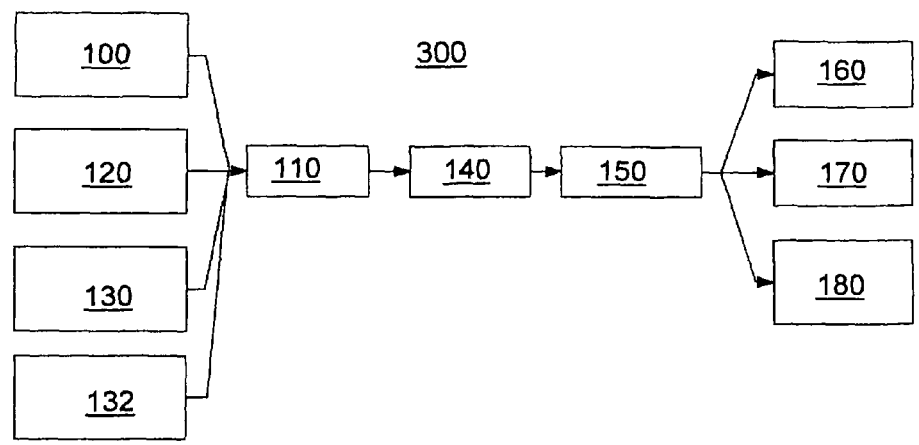
Figure 5:
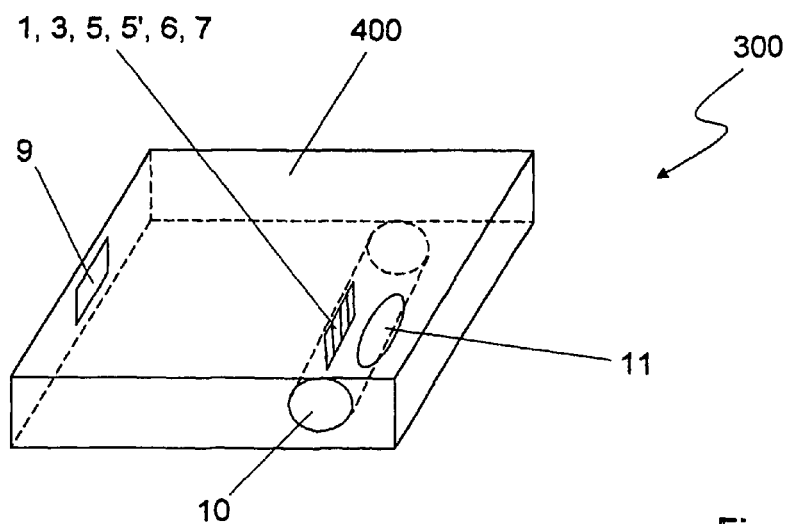
Figure 6:
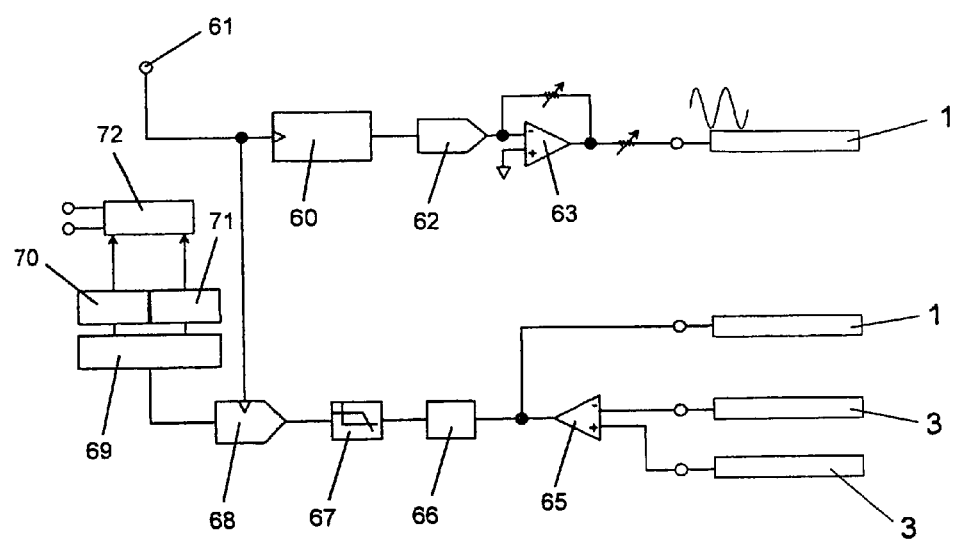

Exemplary embodiments of the invention will be explained in greater detail below, using the drawings. These show:

FIG. 1 schematic view of the impedance measurement unit of the measurement device according to the invention;

FIG. 2 top view of a measurement device according to the invention, as a compact sensor unit;

FIG. 3 measurement device according to the invention, with circular measurement and feed electrodes;

FIG. 4 block diagram of the measurement device according to the invention;

FIG. 5 schematic view of an alternative exemplary embodiment of the measurement device according to the invention;

FIG. 6 block circuit diagram of the impedance measurement unit of the measurement device according to the invention.

The bioelectrical impedance measurement unit 100 of the measurement device according to the invention shown in FIG. 1 comprises two electrodes 1 to feed in electrical alternating current from the power source 2, of variable frequency, and two or more measurement electrodes 3 for an impedance measurement of the body tissue 200 in the region of the finger of the user of the device, in order to determine the local resistance and the local reactance. Because of the four-point measurement, transition resistances between the electrodes 1, 3 and the body tissue 200 do not distort the measurement. It is practical if the distance between the electrodes 1, 3 amounts to only a few millimeters to a few centimeters. During the measurement process, all four electrodes 1, 3 touch the same region of the skin surface on the finger of the user at the same time, for a local determination of the impedance measurement signal. By means of the power source 2, an alternating current of variable frequency is generated. In this manner, measurement of the complex impedance is possible. The measurement signal is detected by means of a voltage meter 4. It is practical if the measurement signal is digitalized by means of an analog/digital converter (not shown in FIG. 1) and afterwards subjected to a discrete Fourier transformation (DFT). The DFT algorithm then yields the real and the imaginary part of the impedance, i.e. the resistance value and the reactance value. The impedance measurement unit 100 shown can be structured to be very compact, if only because of the small distance between electrodes, and thus can easily be integrated into a mobile electronic device (for example wristwatch, mobile telephone, MP3 player, digital camera, handheld, etc.).

FIG. 2 shows the measurement device according to the invention, indicated as a whole as 300, as a compact sensor unit which can be integrated into any desired device. The measurement device 300 has different measurement modalities that are accessible on the interface of a sensor housing 400. The dimensions of the sensor housing 400 amount to only 10×7×3 mm, for example. The user of the measurement device 300 touches it with his fingertips, for example, to carry out a measurement. Light sources 5, 5', for example in the form of light-emitting diodes, are integrated into the measurement device 300, and are able to emit light at different wavelengths. For this purpose, different light-emitting semiconductor elements are accommodated in the common sensor housing 400. It is also possible to use light-wave conductors, in order to guide the light from different light sources to the user interface of the housing 400. Furthermore, the measurement device 300 comprises one or more photosensors 6. The photosensors are disposed in the immediate vicinity of the light source 5 or 5', respectively. The sensors 6 receive the light from the light source 5 or 5' scatted in the tissue on the fingertip of the user. Furthermore, a heat sensor 7 is provided directly next to the light source 5 or 5'. In this way, it is guaranteed that the heat measurement takes place at the same measurement location as the optical measurement. Furthermore, a total of four electrodes 1 or 3, respectively, for measuring the bioelectrical impedance, are provided on the surface of the measurement device 300. The electrodes 1, 3 are separated from one another by means of insulating strips 8. The user of the device touches the four electrodes, i.e. the measurement and feed electrodes, at the same time, with a hand, as was explained above with regard to FIG. 1. At least one of the electrodes indicated with the reference number 1 is furthermore used as an EKG electrode of an EKG unit that is also integrated into the measurement device 300. Another EKG electrode (counter-electrode, not shown) is disposed elsewhere, so that the electrodes can be touched with the fingertips. This results in a two-point derivation (arm to arm measurement).

In the exemplary embodiment of the measurement device 300 shown in FIG. 2, two radiation sources 5 and 5' are provided, which irradiate different volume regions of the body tissue being examined. For this purpose, the two radiation sources 5 and 5' have different spatial emission characteristics, namely different emission angles. The radiation source 5 is a light-emitting diode, while the radiation source 5' is a laser, for example a so-called VCSEL laser (English: "vertical cavity surface emitting laser"). Both the light-emitting diode 5 and the laser 5' emit light having a very similar wavelength (for example 630 nm and 650 nm), but with different aperture angles (for example 25° and 55°). With the array shown in FIG. 2—as explained above—a differential measurement of metabolism-induced changes in the oxygen content in the blood is possible. For this purpose, the wavelength of the radiation emitted by the two radiation sources 5 and 5', in each instance, must lie in a range in which the light is absorbed to different degrees by oxyhemoglobin and deoxyhemoglobin. For an absolute measurement of the oxygen content of the blood (oxygen saturation), other radiation sources (not shown in FIG. 2) must be present, whose wavelength lies in a spectral range in which the light absorption of oxyhemoglobin and deoxyhemoglobin is essentially the same (so-called isosbectic point). The light emitted by the light-emitting diode and the laser, respectively, can be guided to the housing surface of the keyboard by means of corresponding light-guide fibers. In this case, the corresponding fiber ends are shown in FIG. 1 with the reference symbols 5 and 5'. It is possible to couple the light-emitting diode and the laser to the corresponding fibers in such a manner that they emit light into the body tissue to be examined at the desired different aperture angle. Accordingly, different volumes of the body tissue are examined with the two radiation sources. Because of the greater aperture angle, the proportion of the non-perfused epidermis in the body tissue examined by means of the light-emitting diode is greater than in the case of the laser. The light scattered and partly absorbed in the body tissue, both of the radiation source 5 and of the radiation source 5', is detected by means of the sensors 6. The sensors 6 do not have to be disposed directly at the surface of the housing 400. Instead, the light can be passed to the sensors disposed in the interior of the measurement device 300 by means of light-guide fibers. For a differentiation of the light of the radiation source 5 from the light of the radiation source 5', the two light sources 5 and 5' can be operated with different time modulation, whereby the signals detected by means of the sensors 6 are demodulated accordingly. Alternatively it is possible to differentiate the radiation of the two radiation sources 5 and 5' on the basis of the different wavelengths. The radiation intensity of the radiation emitted by the radiation sources 5 and 5' is weakened with the path length when passing through the body tissue, whereby the relationship of the intensity weakening with the concentration of the absorbed substance (oxygenated hemoglobin) is given by the known Lambert-Beer law. By means of the sensors 6 shown in FIG. 2, the parameters of the intensity weakening that are of interest can be determined, specifically separately for the volume regions of the body tissue covered by the radiation sources 5 and 5', in each instance. The parameters of the intensity weakening that are to be assigned to the different radiation sources 5 and 5' can be put into relation with one another by means of a suitably program-controlled evaluation unit, in order to carry out a differentiated measurement in this way. In the simplest case, quotients are calculated, in each instance, from the parameters of the intensity weakening of the radiation of the two radiation sources 5 and 5'. From changes in these quotients, it is then possible to draw conclusions concerning changes in the metabolism. If, for example, the blood glucose level increases after an intake of nutrients, correspondingly more glucose gets into the cells of the body tissue (after a certain time delay) and is converted there. In this connection, oxygen is used up. The cells get this oxygen by way of the blood. In this connection, the oxygenated hemoglobin becomes deoxygenated hemoglobin, by giving off oxygen. Accordingly, the ratio of deoxygenated hemoglobin to oxygenated hemoglobin increases. Because of the different aperture angles of the radiation of the radiation sources 5 and 5', the changes in hemoglobin concentration have different effects on the intensity weakening, in each instance. Thus, changes in the hemoglobin concentration can be detected from the quotient of the parameters of the intensity weakening. This makes it possible to draw a conclusion concerning oxygen consumption indirectly. Since the oxygen consumption in turn depends on the blood glucose level, the blood glucose level can also be determined by means of the differential measurement of the radiation absorption that has been explained. Parallel to the optical measurement, the bioimpedance analysis is carried out by way of the electrodes 1, 3. The purpose of the bioimpedance measurement is primarily the determination of the local perfusion. This is used as an additional parameter in the determination of the oxygen consumption and thus also of the blood glucose level. Different aperture angles of the radiation can also be generated with only one radiation source 5, by means of using corresponding optical elements (for example beam splitters, lenses, etc.).

FIG. 3 shows an alternative embodiment of the measurement device 300 according to the invention with concentrically disposed, essentially circular electrodes 1, 3. Depending on the body location to be examined, the array according to FIG. 2 or the one according to FIG. 3 is better suited.

FIG. 4 schematically shows the structure of the measurement device 300 according to the invention as a block diagram. Measurement device 300 comprises an optical measurement unit 130 for optical measurement of the oxygen concentration in the vascular system of the body tissue at the measurement location, in each instance. The pulse-oximetry signals recorded by means of the optical measurement unit 130 are passed to an analysis unit 110. Another essential component of the measurement device 300 is a heat measurement unit 120 for determining the local heat production. The heat measurement unit 120 is a special heat sensor that insulates the body location being examined, in each instance. This location can therefore only absorb or give off heat by means of the blood stream. For this reason, it is possible to determine the perfusion and the heat production by means of the time-resolved measurement of temperature. In the case of strong perfusion, the body location being examined reaches its maximal temperature in a very short time. In the case of little perfusion, this takes longer. In addition, by way of extrapolation of the measured temperature, it is possible to draw conclusions concerning the arterial temperature, since the temperature at the measurement location is determined only by the arterial temperature and by the local heat production. The measurement signals recorded by the heat measurement unit 120 are also passed to the analysis unit 110 for further processing. Furthermore, the measurement device 300 comprises the impedance measurement unit 100, which serves to detect local tissue parameters by means of a bioelectrical impedance measurement. The measurement signals of the impedance measurement unit 100 are also processed by means of the analysis unit 110. Finally, according to the invention, an EKG unit 132 for detecting an EKG signal is also provided. The EKG unit 132 is also connected with the analysis unit 110, for processing of the EKG signals. The optical measurement unit 130 has the light sources 5, 5' as well as the light sensors 6 of the measurement device 300 shown in FIGS. 2 and 3 assigned to it. The heat measurement unit 120 is connected with the heat sensor 7. The impedance measurement unit 100 detects measurement signals by way of the electrodes 1 and 3, respectively, of the measurement device 300. The analysis unit 110 carries out pre-processing of all the measurement signals. For this purpose, the signals pass through a band-pass filter, in order to filter out interference in the range of the network frequency of 50 or 60 Hz, respectively. Furthermore, the signals are subjected to noise suppression. After passing through the analysis unit 110, the processed signals of the optical measurement unit 130, the heat measurement unit 120, the impedance measurement unit 100 and the EKG unit 132 reach an evaluation unit 140. The evaluation unit 140 is responsible for calculating the parameters essential for the diagnosis from the measurement signals. The functions of the evaluation unit 140 are essentially implemented by means of software. For example, the composition of the body tissue being examined (water content, fat content, etc.) is calculated from the time-dependently recorded measurement signals of the impedance measurement unit 100. The arterial oxygen saturation and—based on the tissue parameters determined previously, on the basis of the impedance measurement—the capillary oxygen saturation are calculated from the signals of the optical measurement unit 130. Furthermore, the perfusion and the arterial temperature are determined from the measurement signals of the heat measurement unit 120 and from the data that can be derived from the time-dependent impedance measurement. The pulse wave velocity is determined from the signals of the EKG unit 132 and those of the optical measurement unit 130. Finally, the venous oxygen saturation, and from it other metabolic parameters, particularly the local oxygen consumption and the glucose concentration at the measurement location, are calculated by means of the evaluation unit 140, from the results of all the calculations carried out previously. The calculation results are interpreted by means of a diagnosis unit 150. The diagnosis unit 150 serves for evaluating the local metabolic parameters calculated by means of the evaluation unit 140. The evaluation unit 140 and the diagnosis unit 150 are connected with a graphics unit 160, to display the measurement results. The data obtained can be stored in a memory unit 170, specifically while simultaneously storing the date and the time of day of the measurement, in each instance. Furthermore, an interface unit 180 is provided, which serves to transmit the calculated physiological parameters. By way of the interface unit 180, all the data and parameters, particularly also the data and parameters stored in the memory unit 170, can be transmitted to a PC of a treating physician, for example, which is not shown in any detail. There, the data can be analyzed in greater detail. In particular, data and parameters recorded with the measurement device 300 over an extended period of time can be investigated with regard to changes, in order to be able to draw conclusions concerning the development of an existing illness from this.

FIG. 5 schematically shows another exemplary embodiment of the measurement device 300 according to the invention. On the outside of the housing 400, an EKG electrode 9 is affixed. This electrode is touched with the finger of one hand. A finger of the other hand is introduced into a tube-like opening 10. In the interior of the opening 10 are the electrodes 1, 3, the light sources 5, 5', the light sensors 6, as well as the heat sensor 7. Furthermore, in the interior of the tube 10, an inflatable air cushion 11 is disposed, which fixes the finger in place and presses it against the sensors gently and with a defined pressure. Operating keys of the measurement device 300 as well as a display to output the measurement results are left out in FIG. 5, for reasons of clarity.

FIG. 6 shows the structure of the impedance measurement unit 100 of the measurement device 300 according to the invention, in terms of circuit technology, as a block diagram. The impedance measurement unit 100 comprises a digital signal generator 60 that has an external cycle signal 61 applied to it. The digital signal is converted to an analog signal by means of a digital/analog converter 62, and amplified by means of an amplifier 63. In this manner, an alternating current signal of variable frequency is generated, which is passed to the body of the patient to be examined by way of the feed electrode 1. The impedance measurement signal is detected by way of a measurement electrode 3 and amplified by means of an amplifier 65. The amplifier 65 is followed by a variable attenuator 66 and a low-pass filter 67 for the purpose of noise suppression. The amplified and filtered analog signal is converted to a digital signal by means of an analog/digital converter 68, and transformed by means of a digital Fourier transformation unit 69. The real part and the imaginary part of the Fourier-transformed measurement signal are stored in registers 70 and 71, respectively. The registers 70 and 71 can be queried by way of an interface 72 (for example PC interface). By way of the interface 72, the Fourier-transformed digital signals are transmitted to the evaluation unit 140 of the measurement device 300 according to the invention.

The invention claimed is:

1. A medical measurement device having an impedance measurement unit having at least one measurement electrode pair comprising a first electrode and a second electrode and at least one feed electrode pair,
    wherein the impedance measurement unit is for detecting an impedance measurement signal on a skin surface of a patient by way of the at least one measurement electrode pair,
    wherein a distance between the first and second electrodes of the at least one measurement electrode pair is within a range of from 1000 micrometers to 1 centimeter, wherein the at least one feed electrode pair comprises a first feed electrode and a second feed electrode for applying an alternating current of variable frequency to a body tissue of the patient, wherein the at least one measurement electrode pair and the at least one feed electrode pair are configured to simultaneously touch a first region of the skin surface, wherein the medical measurement device further comprises a program-controlled evaluation unit connected with the impedance measurement unit, wherein the program-controlled evaluation unit comprises a data processor programmed with software to determine changes in a local impedance measurement signal, and wherein the program-controlled evaluation unit is programmed to determine local resistance and local reactance from the local impedance measurement signal in that the program-controlled evaluation unit comprises an analog/digital converter configured to digitalize the local impedance measurement signal and to subject a digitalized local impedance measurement signal to a discrete Fourier transformation to determine at least one member selected from the group consisting of a heart rate,
a pulse amplitude,
a local perfusion,
a local body temperature, and
a blood glucose level from the changes in the local impedance measurement signal over time caused by an amount of blood changing within a pulse beat.

2. The medical measurement device according to claim 1, wherein the at least one measurement electrode pair and the at least one feed electrode pair are configured as contact strips, and wherein the contact strips are parallel to one another.

3. The medical measurement device according to claim 1, further comprising an EKG unit for detecting an EKG signal by way of two or more EKG electrodes.

4. The medical measurement device according to claim 3, wherein at least one EKG electrode of the two or more EKG electrodes is simultaneously a member selected from the group consisting of: the first feed electrode of the at least one feed electrode pair, the second feed electrode of the at least one feed electrode pair, the first electrode of the at least one measurement electrode pair, and the second electrode of the at least one measurement electrode pair.

5. The medical measurement device according to claim 1, further comprising:
an optical measurement unit comprising at least one radiation source for irradiating body tissue, and
at least one radiation sensor for detection of radiation scattered and/or transmitted by the body tissue.

6. The medical measurement device according to claim 5, wherein the optical measurement unit has at least two radiation sensors for detection of the radiation scattered and/or transmitted by the body tissue, and wherein the at least two radiation sensors are disposed at different distances from the at least one radiation source.

7. The medical measurement device according to claim 5, wherein the at least one radiation source comprises at least two radiation sources, wherein a first radiation source of the at least two radiation sources can irradiate a first volume region of the body tissue, wherein a second radiation source of the at least two radiation sources can irradiate a second volume region of the body tissue, and wherein the first volume region is different from the second volume region.

8. The medical measurement device according to claim 7, wherein the at least two radiation sources have different spatial emission characteristics.

9. The medical measurement device according to claim 5, further comprising a light-conducting element connected with the at least one radiation source, wherein the at least one radiation source can emit radiation to the skin surface, and wherein the light-conducting element can guide the radiation emitted by the at least one radiation source to the skin surface.

10. The medical measurement device according to claim 1, further comprising a temperature or heat sensor.

11. The medical measurement device according to claim 1, further comprising a fixation device for fixation of a body part of a patient on the medical measurement device.

12. The medical measurement device according to claim 11, wherein the fixation device comprises an inflatable air cushion, and wherein the inflatable air cushion can press the body part against the first and second electrodes of the at least one measurement electrode pair and/or feed electrodes of the at least one feed electrode pair.

13. The medical measurement device according to claim 1, further comprising a plurality of feed and/or measurement electrodes of the impedance measurement unit, wherein the plurality of feed and/or measurement electrodes of the impedance measurement unit are disposed in a matrix.

14. An electronic device comprising:
a medical measurement device having an impedance measurement unit having at least one measurement electrode pair comprising a first electrode and a second electrode and at least one feed electrode pair, and
an entertainment device or communications technology device connected with the medical measurement device, wherein the impedance measurement unit is for detecting an impedance measurement signal on a skin surface of a patient, by way of the at least one measurement electrode pair, wherein a distance between the first and second electrodes of the at least one measurement electrode pair is within a range of from 1000 micrometers to 1 centimeter, wherein the at least one feed electrode pair comprises a first feed electrode and a second feed electrode for applying an alternating current of variable frequency to a body tissue of the patient, wherein the at least one measurement electrode pair and the at least one feed electrode pair are configured to simultaneously touch a first region of the skin surface, wherein the medical measurement device further comprises a program-controlled evaluation unit connected with the impedance measurement unit, wherein the program-controlled evaluation unit comprises a data processor programmed with software to determine changes in a local impedance measurement signal, and wherein the program-controlled evaluation unit is programmed to determine local resistance and local reactance from the local impedance measurement signal in that the program-controlled evaluation unit comprises an analog/digital converter configured to digitalize the local impedance measurement signal and to subject a digitalized local impedance measurement signal to a discrete Fourier transformation to determine at least one member selected from the group consisting of
a heart rate,
a pulse amplitude,
a local perfusion,
a local body temperature, and
a blood glucose level
from the changes in the local impedance measurement signal over time caused by an amount of blood changing within a pulse beat.

15. The electronic device according to claim 14, wherein the entertainment device or communications technology device is a mobile device.

16. A medical measurement device having an impedance measurement unit having at least one measurement electrode pair comprising a first electrode and a second electrode and at least one feed electrode pair,
wherein the impedance measurement unit is for detecting an impedance measurement signal on a skin surface of a patient by way of the at least one measurement electrode pair,
wherein a distance between the first and second electrodes of the at least one measurement electrode pair is within a range of from 1000 micrometers to 1 centimeter,
wherein the at least one feed electrode pair comprises a first feed electrode and a second feed electrode for applying an alternating current of variable frequency to a body tissue of the patient,
wherein the at least one measurement electrode pair and the at least one feed electrode pair are configured to simultaneously touch a first region of the skin surface,
wherein the medical measurement device further comprises a program-controlled evaluation unit connected with the impedance measurement unit,
wherein the program-controlled evaluation unit comprises a data processor programmed with software to determine changes in a local impedance measurement signal over time caused by an amount of blood changing within a pulse beat, and
wherein the program-controlled evaluation unit is configured to determine local resistance and local reactance from the local impedance measurement signal in that:
the program-controlled evaluation unit comprises an analog/digital converter configured to digitalize the local impedance measurement signal, and
the program-controlled evaluation unit is programmed to subject a digitalized local impedance measurement signal to a discrete Fourier transformation.

* * * * *